US012697345B2

(12) United States Patent
Bleiel

(10) Patent No.: US 12,697,345 B2
(45) Date of Patent: Aug. 4, 2026

(54) MICROPARTICLES CONTAINING STABILIZED CBD OIL, AND METHODS FOR THE PRODUCTION THEREOF

(71) Applicant: Anabio Technologies Limited, Dublin (IE)

(72) Inventor: Sinead Bleiel, Dublin (IE)

(73) Assignee: Anabio Technologies Limited, Dublin (IE)

( * ) Notice: Subject to any disclaimer, the term of this patent is extended or adjusted under 35 U.S.C. 154(b) by 173 days.

(21) Appl. No.: 18/284,283

(22) PCT Filed: Mar. 28, 2022

(86) PCT No.: PCT/EP2022/058174
§ 371 (c)(1),
(2) Date: Sep. 26, 2023

(87) PCT Pub. No.: WO2022/200635
PCT Pub. Date: Sep. 29, 2022

(65) Prior Publication Data
US 2024/0066041 A1 Feb. 29, 2024

(30) Foreign Application Priority Data

Mar. 26, 2021 (GB) .................................. 2104350.0
Mar. 26, 2021 (GB) .................................. 2104355.9

(51) Int. Cl.
| | |
|---|---|
| *A23L 29/30* | (2016.01) |
| *A23D 9/007* | (2006.01) |
| *A23D 9/05* | (2006.01) |
| *A23G 3/40* | (2006.01) |
| *A23G 3/42* | (2006.01) |
| *A23G 3/48* | (2006.01) |
| *A23L 2/52* | (2006.01) |
| *A23L 33/105* | (2016.01) |
| *A23L 33/115* | (2016.01) |
| *A61K 9/00* | (2006.01) |
| *A61K 9/107* | (2006.01) |
| *A61K 9/16* | (2006.01) |
| *A61K 9/48* | (2006.01) |
| *A61K 31/00* | (2006.01) |
| *A61K 36/185* | (2006.01) |

(52) U.S. Cl.
CPC ............ *A61K 31/658* (2023.05); *A23D 9/007* (2013.01); *A23D 9/05* (2013.01); *A23G 3/40* (2013.01); *A23G 3/42* (2013.01); *A23G 3/48* (2013.01); *A23L 2/52* (2013.01); *A23L 29/35* (2016.08); *A23L 33/105* (2016.08); *A23L 33/115* (2016.08); *A61K 9/0095* (2013.01); *A61K 9/1075* (2013.01); *A61K 9/1652* (2013.01); *A61K 9/1664* (2013.01); *A61K 9/1694* (2013.01); *A61K 9/4808* (2013.01); *A61K 36/3482* (2024.05)

(58) Field of Classification Search
CPC .. A61K 31/658; A61K 9/0095; A61K 9/1075; A61K 9/1652; A61K 9/1664; A61K 9/1694; A61K 9/4808; A61K 36/3482; A23L 29/35; A23L 33/105; A23L 33/115; A23L 2/52; A23D 9/007; A23D 9/05; A23G 3/40; A23G 3/42; A23G 3/48
See application file for complete search history.

(56) References Cited

U.S. PATENT DOCUMENTS

| | | |
|---|---|---|
| 2020/0170950 A1 | 6/2020 | Adair et al. |
| 2021/0077394 A1 | 3/2021 | Moaseri |

FOREIGN PATENT DOCUMENTS

| | | | |
|---|---|---|---|
| CN | 201410108919 | * | 7/2014 |
| WO | 2017127641 A1 | | 7/2017 |
| WO | 2020247638 A1 | | 12/2020 |

OTHER PUBLICATIONS

International Search Report from International Application No. PCT/EP2022/058174, date mailed: Jul. 18, 2022.

* cited by examiner

*Primary Examiner* — Shirley V Gembeh
(74) *Attorney, Agent, or Firm* — Morse, Barnes-Brown & Pendleton, P.C.; Russell L. Widom

(57) ABSTRACT

Food, beverage and nutritional supplements containing microparticles containing stabilised CBD oil, and methods for the production thereof" Food, beverage and nutritional supplements that containing microparticles are described. The microparticles contain CBD oil stabilized in an acacia or inulin fibre or cyclodextrin matrix. Methods for the production of the compositions comprise making the microparticles by providing an oil-in-water microemulsion comprising CBD oil, water, acacia/inulin fibre and optionally maltodextrin or cyclodextrin, and freeze-drying the microemulsion to remove water and provide a preparation of dried microparticles. The dried microparticles comprise a dispersed phase of stabilized microdroplets of CBD oil disposed in a continuous solid matrix comprising acacia or inulin fibre. The preparation of microcapsules contains less than 10% free CBD oil and exhibit improved pharmacokinetics and bioavailability of CD.

19 Claims, 10 Drawing Sheets

| Compound | Result (%) | Result (mg/g) |
|---|---|---|
| Cannabidiolic acid (CBD-A) | N.D | N.D |
| Cannabigerol (CBG) | 0.27 | 2.75 |
| Cannabidiol (CBD) | 4.67 | 46.70 |
| Tetrahydrocannabivarin (THC-V) | N.D | N.D |
| Cannabinol (CBN) | N.D | N.D |
| Delta-9-Tetrahydrocannabinol (9-THC) | N.D | N.D |
| Delta-8-Tetrahydrocannabinol (8-THC) | N.D | N.D |
| Tetrahydrocannabinolic acid (THC-A) | N.D | N.D |
| Total Cannabinoids | 4.94% | 49.45 mg/g |

Fig. 6A

MICROPARTICLES CONTAINING STABILIZED CBD OIL, AND METHODS FOR THE PRODUCTION THEREOF

CROSS-REFERENCE TO RELATED APPLICATIONS

This application is a national stage filing under 35 U.S.C. 371 of International Application No. PCT/EP2022/058174, filed Mar. 28, 2022, which claims the priority of GB 2104350.0 and GB 2104355.9, both filed on Mar. 26, 2021. The entire teachings of said applications are incorporated herein by reference.

TECHNICAL FIELD

The invention relates to microparticles containing stabilised CBD oil, and methods for the production thereof.

BACKGROUND TO THE INVENTION

Hemp oil is recognized for its medicinal and nutritional qualities, partly due to the high amounts of cannabinoids, including cannabidiol (CBD), which have been indicated for numerous conditions including pain associated with multiple sclerosis, inflammatory conditions, and epilepsy. The development of an oral formulation of Hemp Oil/cannabinoids for mammals is hindered by Hemp Oil's low oral bioavailability. This means that, when given orally, very little CBD reaches the bloodstream. The reason for this is that Hemp Oil and CBD are highly susceptible to oxidation and enzymatic degradation in the gastrointestinal tract and has very low permeability across the gut wall. A further problem associated with hemp oil products is the small and taste of the oil, and the difficulty providing hemp oil in a form in which it can be easily incorporated into aqueous products.

WO02/064109 describes process for extraction of pharmaceutically active cannabinoids from plant material followed by cold filtration, decarboxylation and purification.

WO02/092217 described microcapsules containing a mixture of at least one solubilised vegetable protein and a polyelectrolyte with an opposite charge to the protein, that are subjected to coacervation in an aqueous medium.

WO2012/038061 describes polymeric nanocapsules containing microemulsions of water in oil and at least one hydrophilic active ingredient dissolved in the aqueous phase.

EP0856355 describes enzymatic crosslinking of protein-encapsulated oil particles by complex coacervation.

U.S. Pat. No. 5,271,961 describes protein microspheres formed by phase separation in a non-solvent followed by solvent removal.

WO2016/193373 describes a solution to the problem of stabilizing oils in food products by providing a cold gelation method of encapsulating and stabilizing the oil. The method comprises providing a microemulsion of oil, protein and sugar, encapsulating droplets of the microemulsion inside a chitosan shell, and polymerizing the core-shell microcapsule in a gelation bath before drying of the microcapsules. The core-shell microcapsules of this method provide oil is a stabilized form that can safely transit the stomach and degrade to release the oil in the ileum. The chitosan shell also masks the smell of the encapsulated oils. While the process is a good technical solution, it can be expensive due to the cold-gelation methods, and the amount of free (un-encapsulated oil) present in the product is rarely below 10% by volume.

WHO dossier (*Cannabidiol Expert Committee on Drug Dependence* 39th *ECDD* (2017) *Agenda item* 5.2) outlines that oral delivery of an oil-based capsule formulation of CBD has been assessed in human with low bioavailability results, due to its poor aqueous solubility and absorption of CBD from the gastrointestinal tract. These weakness result in a poor pharmacokinetic profile is variable absorption rates and no therapeutic effect. Bioavailability from oral delivery of CBD is estimated to be 6% due these absorption issue in the mammal which is linked to significant first-pass metabolism (REFERENCE: Hawksworth, G. and K. McArdle, *Metabolism and pharmacokinetics of cannabinoids.* The Medicinal Uses of *Cannabis* and Cannabinoids. Pharmaceutical Press, London, 2004: p. 205-228.) In healthy male volunteers, the mean±S D whole blood levels of CBD at 1, 2 and 3 hours after administration of 600 mg oral CBD were reported to be 0.36 (0.64) ng/mL, 1.62 (2.98) ng/mL and 3.4 (6.42) ng/mL, respectively (REFERENCE: Martin-Santos, R., et al., *Acute effects of a single, oral dose of d9-tetrahydrocannabinol (THC) and cannabidiol (CBD) administration in healthy volunteers.* Curr Pharm Des, 2012. 18(32): p. 4966-79).

Aerosolized CBD has been reported to yield rapid peak plasma concentrations in 5-10 minutes and higher bioavailability than oral administration; however significant dose responses from 10 mg-200 mg have not been reported. Due to weak pharmakinetic character, CBD requires stabilisation for delivery through the gastrointestinal tract and further requires a chaperon to aid absorption across the gut wall without significant loss or damage to the molecule.

It is an object of the invention to overcome at least one of the above-referenced problems. In particular, it is an object of the invention to provide a food ingredient in a powder form that contains CBD oil that is stable to oxidation and contains low amounts of free oil. It is another object of the invention to provide a process for producing a food ingredient that is less expensive and energy intensive than the prior art.

It is another object of the invention to provide a greater bioavailability of CBD for improved dose response for therapeutic effects via encapsulation technology.

SUMMARY OF THE INVENTION

The Applicant has addressed the problems of the prior art by providing a method of making a food, beverage or nutritional supplement composition comprising microparticles containing stabilized CBD oil that results in a microparticle preparation with very low amounts of free CBD oil (typically less than 10% by volume). In addition, the encapsulation of the CBD oil improved the bioavailability and reduced the ESR (erythrocyte sedimentation rate) values compared to CBD packaged in liposomal formulations (FIGS. 11 and 12). The method is also less expensive and energy intensive that the cold gelation methods of the prior art. The method comprises making a microemulsion of CBD oil, water and a soluble fibre such as acacia or inulin (and/or cyclodextrin), and processing the microemulsion by freeze-drying and size-reduction to provide a preparation of microparticles (e.g. a powder) that contains very low amounts of free CBD oil. The microparticles are gastric resistant and ileal sensitive and comprise microdroplets of CBD oil stabilized within a continuous cyclodextrin matrix. Addition of maltodextrin has been found to improve the water dispersibility of the microparticles allowing the microparticles to be formulated in aqueous beverages. The preparation of microparticles may be combined with other ingredients to form a food, beverage or nutritional supplement composition.

In a first aspect, the invention provides a method of making a food, beverage or nutritional supplement composition comprising a preparation of gastro-resistant, ileal-sensitive microparticles, the method comprising the steps of:

providing an oil-in-water microemulsion comprising an aqueous phase and a solid phase comprising CBD oil and a matrix forming material selected from acacia fibre, inulin or a cyclodextrin; and freeze-drying the microemulsion to remove water and provide a solid cake and size-reducing the solid cake to provide a preparation of dried microparticles.

The dried microparticles generally comprise a dispersed phase of stabilized microdroplets of CBD oil disposed in a continuous solid matrix comprising acacia fibre, inulin fibre or cyclodextrin.

In any embodiment, the matrix forming material is a soluble fibre such as, for example inulin or acacia fibre.

In any embodiment, the matrix forming material is a cyclodextrin.

In any embodiment, the oil in water emulsion comprises an emulsifier.

In any embodiment, the preparation of microcapsules contains less than 10% free CBD oil.

Typically, size reduction of the cake comprises shredding grinding of the cake.

In any embodiment, the microemulsion comprises 10-70% of the solid phase and 30-90% of the aqueous phase (w/w).

In any embodiment, the microemulsion comprises 10-70% of the solid phase and 30-90% of the aqueous phase (w/w). In any embodiment, the microemulsion comprises 20-30% of the solid phase and 70-80% of the aqueous phase (w/w).

In any embodiment, the solid phase comprises an oligosaccharide filler. The oligosaccharide filler may be for example maltodextrin or a cyclodextrin. The filler may constitute 2-20% or 4-15% of the solid phase by weight.

In any embodiment, the solid phase comprises maltodextrin. In any embodiment, the solid phase comprises 5-15% or 5-10% of maltodextrin.

In any embodiment, the solid phase comprises acacia or inulin fibre and cyclodextrin. In any embodiment, the weight ratio of fibre to cyclodextrin is at least 2:1 (for example 3:1 or 4:1).

In any embodiment, the solid phase comprises maltodextrin and cyclodextrin.

In any embodiment, the microemulsion comprises 25-45% of the solid phase and 55-75% of the aqueous phase (w/w).

In any embodiment, the solid phase comprises (or consists essentially of) CBD oil, cyclodextrin and/or a fibre (e.g. acacia or inulin), emulsifier, optionally protein, optionally maltodextrin and optionally a divalent metal ion salt. Maltodextrin has been found to improve the water dispersibility of the resultant powder. A divalent metal ion salt such as a calcium citrate has been found to reduce the free oil content of the powder.

In any embodiment, the solid phase comprises:
   10-90% CBD oil;
   10-90% cyclodextrin or acacia/inulin fibre and optionally including protein; and
   0.1 to 5% emulsifier.

In any embodiment, the solid phase comprises:
   30-40% CBD oil;
   60-70% cyclodextrin optionally including protein; and
   0.5 to 2% emulsifier.
   In any embodiment, the solid phase comprises:
   30-40% CBD oil;
   60-70% cyclodextrin optionally including protein; and
   0.5 to 2% emulsifier.
   In any embodiment, the solid phase comprises (w/w):
   to 80% acacia or inulin fibre;
   to 80% CBD oil; and
   1 to 20% maltodextrin.
   In any embodiment, the solid phase comprises (w/w):
   to 60% acacia or inulin fibre;
   to 75% CBD oil; and
   4 to 16% maltodextrin.

In any embodiment, the solid phase comprises 5-20% (w/w) protein. The protein may be native or denatured.

In any embodiment, the solid phase comprises 1-5% (w/w) divalent metal ion salt. The salt may be a citrate. The metal ion may be calcium, magnesium or iron.

In any embodiment, the microemulsion consists essentially of water, CBD oil, acacia or inulin fibre and/or cyclodextrin, optionally protein, and optionally a filler.

In any embodiment, the microemulsion consists essentially of water, CBD oil, acacia fibre and a filler.

In any embodiment, the microemulsion consists essentially of water, CBD oil, acacia fibre and maltodextrin.

In any embodiment, the microemulsion consists essentially of water, CBD oil, acacia fibre, maltodextrin and cyclodextrin.

In any embodiment, the microemulsion consists essentially of water, CBD oil, emulsifier, and cyclodextrin.

In any embodiment, the microemulsion consists essentially of water, CBD oil, emulsifier, cyclodextrin, and a filler such as protein or a sugar-based excipient such as maltodextrin.

In any embodiment, the microemulsion consists essentially of water, CBD oil, emulsifier, cyclodextrin, and a divalent metal ion salt.

In any embodiment, the microemulsion consists essentially of water, CBD oil, emulsifier, cyclodextrin, and one or more additional components selected from protein, maltodextrin and a divalent metal ion salt.

In any embodiment, the oil-in-water microemulsion is formed by a process comprising the steps of:

combining water with a matrix forming material selected from acacia or inulin fibre and cyclodextrin and allowing the matrix forming material to hydrate;

homogenizing the hydrated matrix forming material;

adding the CBD oil to the homogenized hydrated matrix forming material; homogenizing the mixture allowing the homogenized mixture to rest for specified time period (for example 5-30 minutes);

further homogenizing the mixture; and allowing the further homogenized mixture to rest.

In any embodiment, the matrix forming material is acacia fibre. In any embodiment, the matrix forming material is cyclodextrin. In any embodiment, the matrix forming material is acacia fibre and cyclodextrin.

In any embodiment, the mixture is homogenised and allowed to rest in an iterative manner. In any embodiment, the process comprises at least 3, 4 or 5 rounds of homogenisation following by a resting step.

In any embodiment, the homogenisation pressure during the rounds of homogenization/resting is alternated between low pressure (e.g. 30-70 Pa) and high pressure (e.g. 130-170 Pa). Thus, the pressure during the first round of homogenization may be 50 Pas, and then 150 Pas for the second round, and then 50 Pas for the third round etc.

In any embodiment, the water is heated to at least at 25° C., 40° C., 50° C. or 55° C.

In any embodiment, the CBD oil is added to the homogenized hydrated acacia fibre in a drop-by-drop manner, typically during mixing.

In any embodiment, the method comprises three rounds of triple homogenisation processes followed by resting.

In any embodiment, each resting step last for at least 5 minutes and is generally 5-30 minutes depending on the volume of microemulsion being processed.

In any embodiment, the suspension/mixture is rested at room temperature.

In any embodiment, the microemulsions comprises a filler, in which the method comprises adding the filler to the hydrated fibre and homogenizing the hydrated fibre and filler suspension.

In any embodiment, the homogenisation is performed using an in-tank or in-line three stage homogenizer with the capability to generate high shear rates.

In a further aspect, the invention provides a food, beverage or nutritional supplement composition comprising a preparation of gastro-resistant, ileal-sensitive microparticles and formed according to a method of the invention.

In a further aspect, the invention provides a food, beverage or nutritional supplement comprising microparticles, in which the microparticles comprise CBD oil, fibre (inulin or acacia) or cyclodextrin and optionally a filler and less than 5% water by weight, in which the CBDoil is provided as stabilized CBD oil microdroplets distributed throughout a continuous solid matrix comprising fibre or cyclodextrin and optionally a filler.

In any embodiment, the continuous solid matrix comprises acacia or inulin fibre. In any embodiment, the continuous solid matrix comprises cyclodextrin. In any embodiment, the continuous solid matrix comprises acacia or inulin fibre and cyclodextrin.

In any embodiment, the microparticle comprises 1-20% CBD oil by weight. In any embodiment, the microparticle comprises 3-13% CBD oil by weight. In any embodiment, the microparticle comprises about 5-10% CBD oil by weight.

In any embodiment, the microparticles have an average dimension of 80-500 microns. In any embodiment, the microparticles have an average dimension of 100-450 microns. In any embodiment, the microparticles have an average dimension of 150-200 microns. In any embodiment, the microparticles have an average dimension of 250-450 microns. In any embodiment, the microparticles have an average dimension of 250-350 microns. In any embodiment, the microparticles have an average dimension of 350-450 microns.

In any embodiment, the continuous solid matrix comprises filler, in which a weight ratio of fibre to filler is at least 2:1.

In any embodiment, the microparticle consists essentially of CBD oil, optionally emulsifier, optionally protein, and fibre (e.g. inulin or acacia) or cyclodextrtin.

In any embodiment, the microparticle consists essentially of CBD oil, acacia fibre or cyclodextrtin, optionally emulsifier, and optionally protein.

In any embodiment, the microparticle consists essentially of CBD oil, acacia fibre, and maltodextrin.

In any embodiment, the microparticle consists essentially of CBD oil, acacia fibre, and cyclodextrin.

In any embodiment, the microparticle consists essentially of CBD oil, acacia fibre, cyclodextrin and maltodextrin.

In any embodiment, the continuous solid matrix comprises protein, in which a weight ratio of cyclodextrin to protein is 3:1 to 1:3, or 2:1 to 1:2, or preferably 2:1 to 1:1.

In any embodiment, the microparticle comprises (or consists essentially of) water, CBD oil, cyclodextrin, emulsifier, optionally protein, optionally maltodextrin and optionally a divalent metal ion salt.

In any embodiment, the microparticle comprises 1-5% (w/w) divalent metal ion salt. The salt may be a citrate. The metal ion may be calcium, magnesium or iron.

In any embodiment, the microparticle consists essentially of CBD oil, cyclodextrin, emulsifier and optionally protein (or another filler) in which a weight ratio of cyclodextrin to protein (or filler) is at least 2:1 (e.g. 3:1 or 4:1).

In any embodiment, the microparticle comprises (w/w):
10 to 90% acacia or inulin fibre or cyclodextrin;
10 to 90% CBD oil.
In any embodiment, the microparticle comprises (w/w):
20 to 80% acacia or inulin fibre or cyclodextrin;
20 to 80% CBD oil; and
1 to 20% maltodextrin.
In any embodiment, the microparticle comprises (w/w):
20 to 60% acacia or inulin fibre or cyclodextrin;
20 to 75% CBD oil; and
4 to 16% maltodextrin.
In any embodiment, the microparticle comprises (w/w):
10 to 90% acacia or inulin fibre;
10 to 90% CBD oil.
In any embodiment, the microparticle comprises (w/w):
20 to 80% acacia or inulin fibre;
20 to 80% CBD oil; and
1 to 20% maltodextrin.
In any embodiment, the microparticle comprises (w/w):
20 to 60% acacia or inulin fibre;
25 to 75% CBD oil; and
4 to 16% maltodextrin.
In any embodiment, the microparticle comprises (or consists essentially of) (w/v):
20 to 75% cyclodextrin;
0.1 to 5.0% emulsifier;
20 to 75% CBD oil; and
less than 1% water.
In any embodiment, the microparticle comprises (or consists essentially of) (w/v):
53 to 70% cyclodextrin;
0.1 to 2.0% emulsifier;
28 to 45% CBD oil; and
less than 1% water.
In any embodiment, the microparticle consists essentially of water, CBD oil, emulsifier, cyclodextrin, and a divalent metal ion salt.

In any embodiment, the microemulsion consists essentially of water, CBD oil, emulsifier, cyclodextrin, and one or more additional components selected from protein, maltodextrin and a divalent metal ion salt.

In any embodiment, free CBD oil constitutes less than 10% by weight of the microparticles.

In any embodiment, free CBD oil constitutes less than 8%, 7% or 6% by weight of the microparticles.

The beverage may be an aqueous beverage, and may contain 1-20%, 1-10%, 5-15% of the microparticles (w/v). The microparticles may be fully dispersible in the beverage.

Other aspects and preferred embodiments of the invention are defined and described in the other claims set out below.

Figure 1A:
FIG. 1a. Chemical structure off Cannabidiol.
Figure 1B:

CAS 13956-29-1. IUPAC Name: 2-[(6R)-3-methyl-6-prop-1-en-2-ylcyclohex-2-en-1-yl]-5-pentylbenzene-1,3-diol Molecular Formula: $C_{21}H_{30}O_2$ Molecular Weight: 314.469 g/mol FIG. 1b. Micro-emulsion as per Hemp Oil formulation in Table 5

Figure 2:
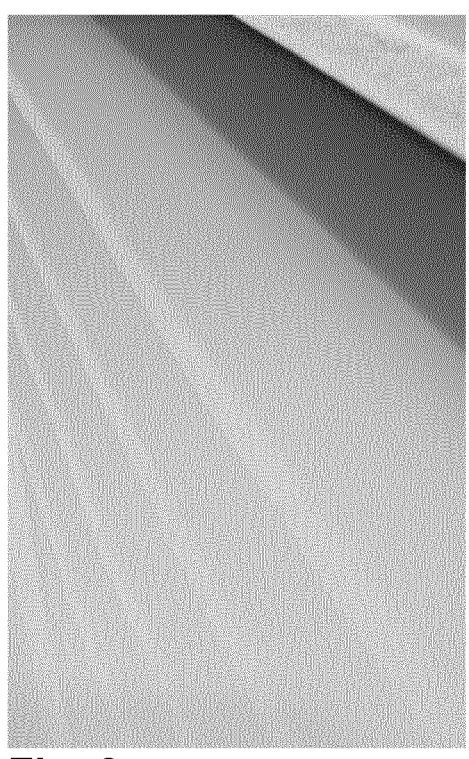

FIG. 2. Microemulsion visual inspection before freeze-drying—left image shows Micro-emulsion as per Table 2 (FIG. 2a). Image on right shows micro-emulsion as per Table 1 (FIG. 2b).

Figure 3:
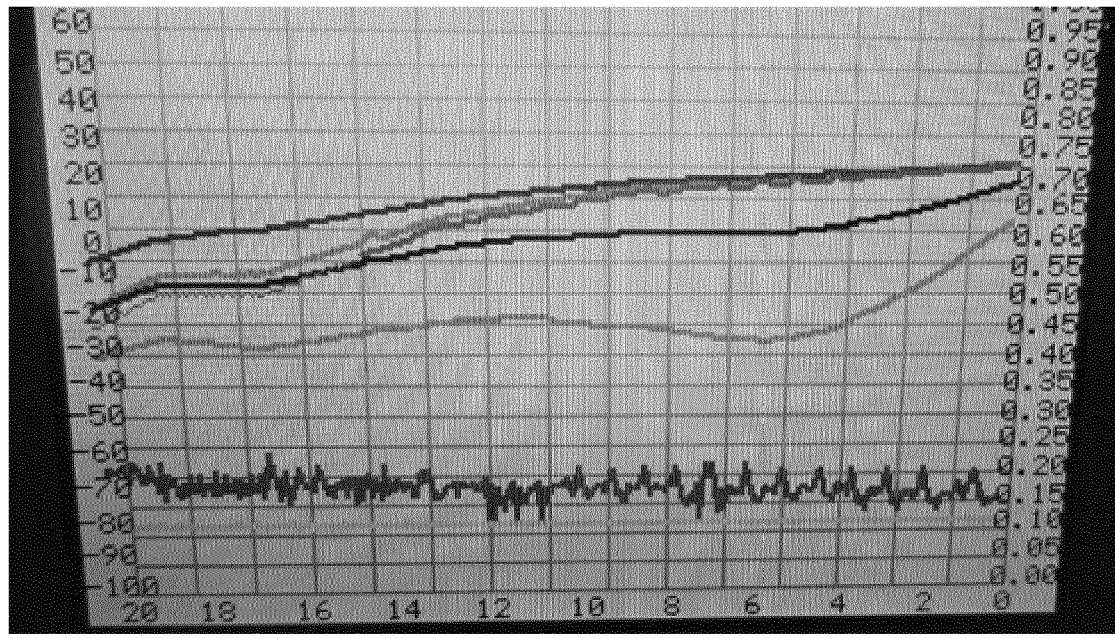

FIG. 3. illustrates trends for drying process (Yellow=Chamber vacuum; Red=Fluid (shelf) temperature; Blue=Condenser temperature and green=Product temperature.

Figure 4:

FIG. 4. Image of Freeze-dried cake after 72 hour drying using cyclodextrin formulation (as per table 2, 4, 6, 8, 9, 10 or 11)

Figure 5:
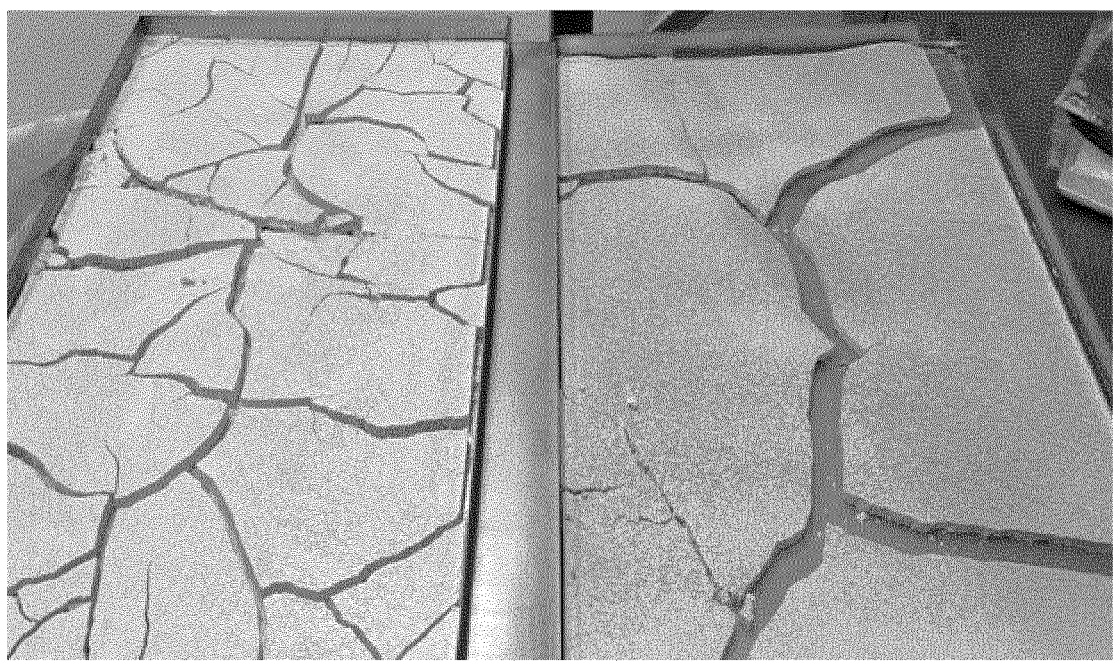

FIG. 5. shows difference in colour of formulations with (FIG. 5a) and without (FIG. 5b) oligosaccharide. Image on the left represents the colour of the microemulsion recipe presented in Table 4, 6, 8, 9, 10 or 11. Image on the right represents the microemulsion recipes presented in Table 3, 5 or 7.

FIG. 6A. Summary of HPLC chromatographic results for micro-encapsulated CBD after extraction and release from the encapsulated matrix (as per micro emulsion shown in Table 3, 5 or 7.

Figure 6B:
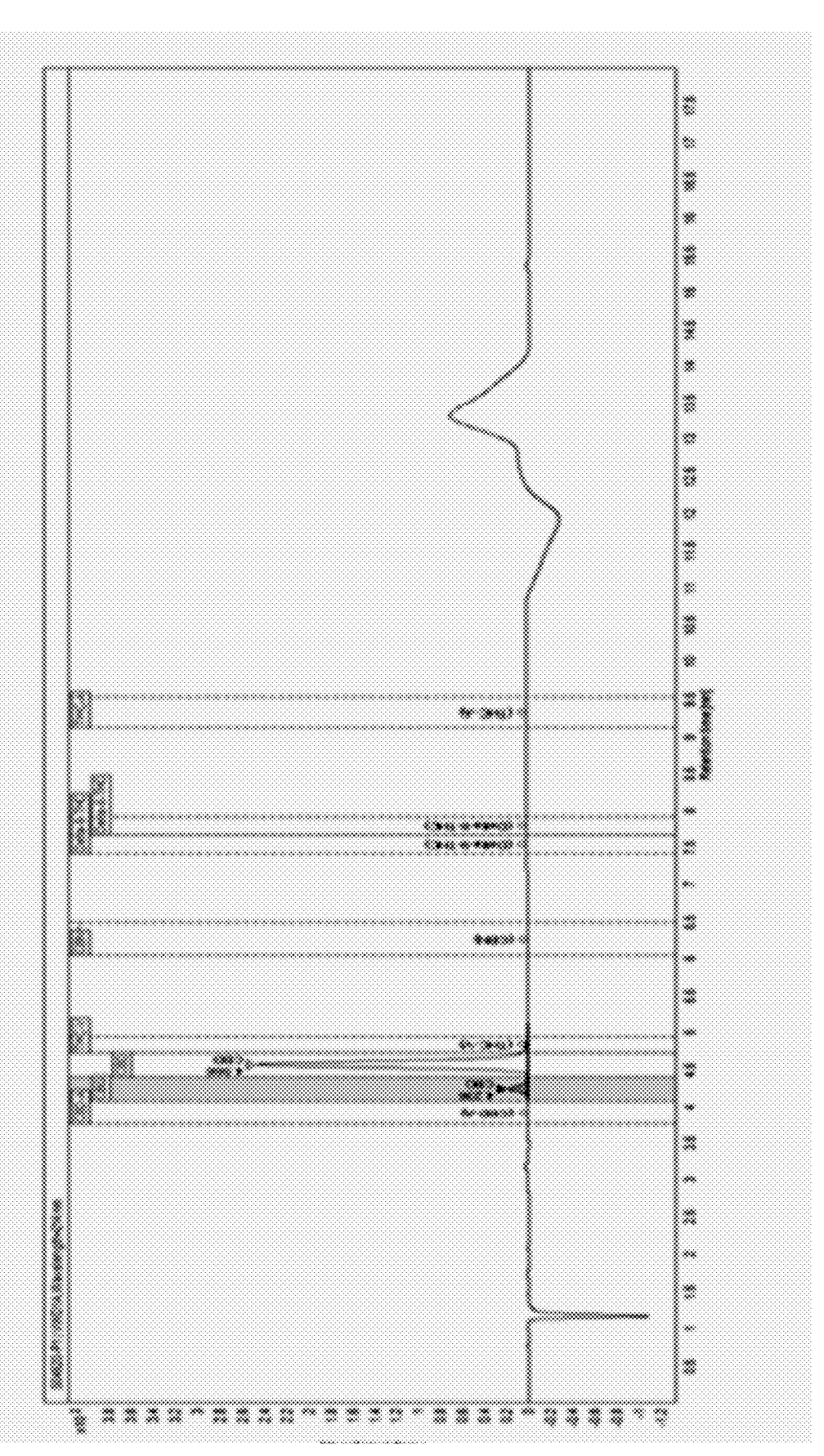

FIG. 6B. HPLC chromatographic results for 5% total CBD content in micro-encapsulated Hemp oil materials after extraction and release from the encapsulated matrix (as per micro emulsions shown in Table 3 and 4).

Figure 7A:
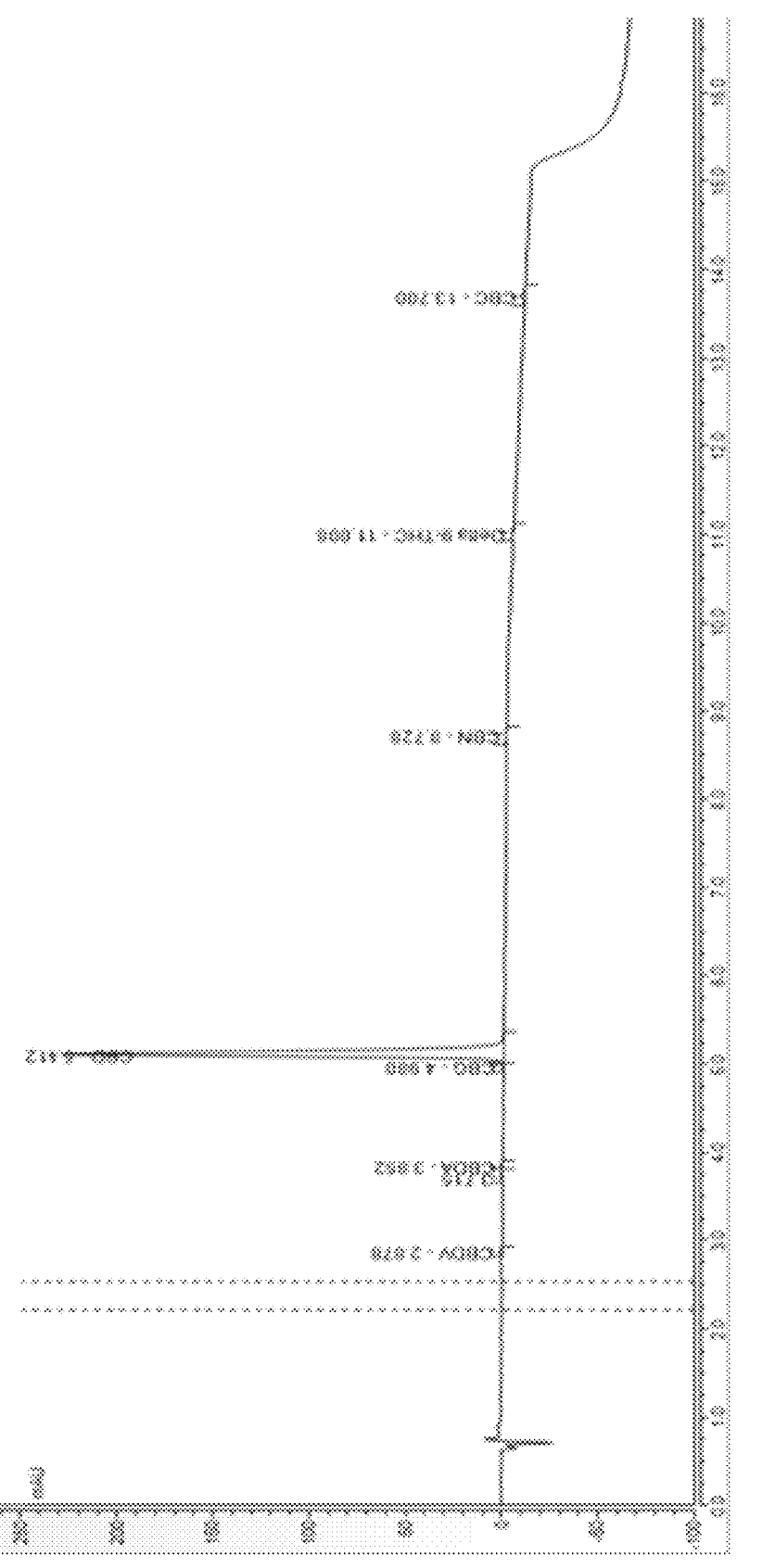

FIG. 7A. Typical HPLC chromatographic results for 10% total CBD content in micro-encapsulated Hemp oil materials of undiluted digested samples after extraction and release from the encapsulated matrix (as per micro emulsion shown in Table 5, 6, 7 and 8).

Figure 7B:
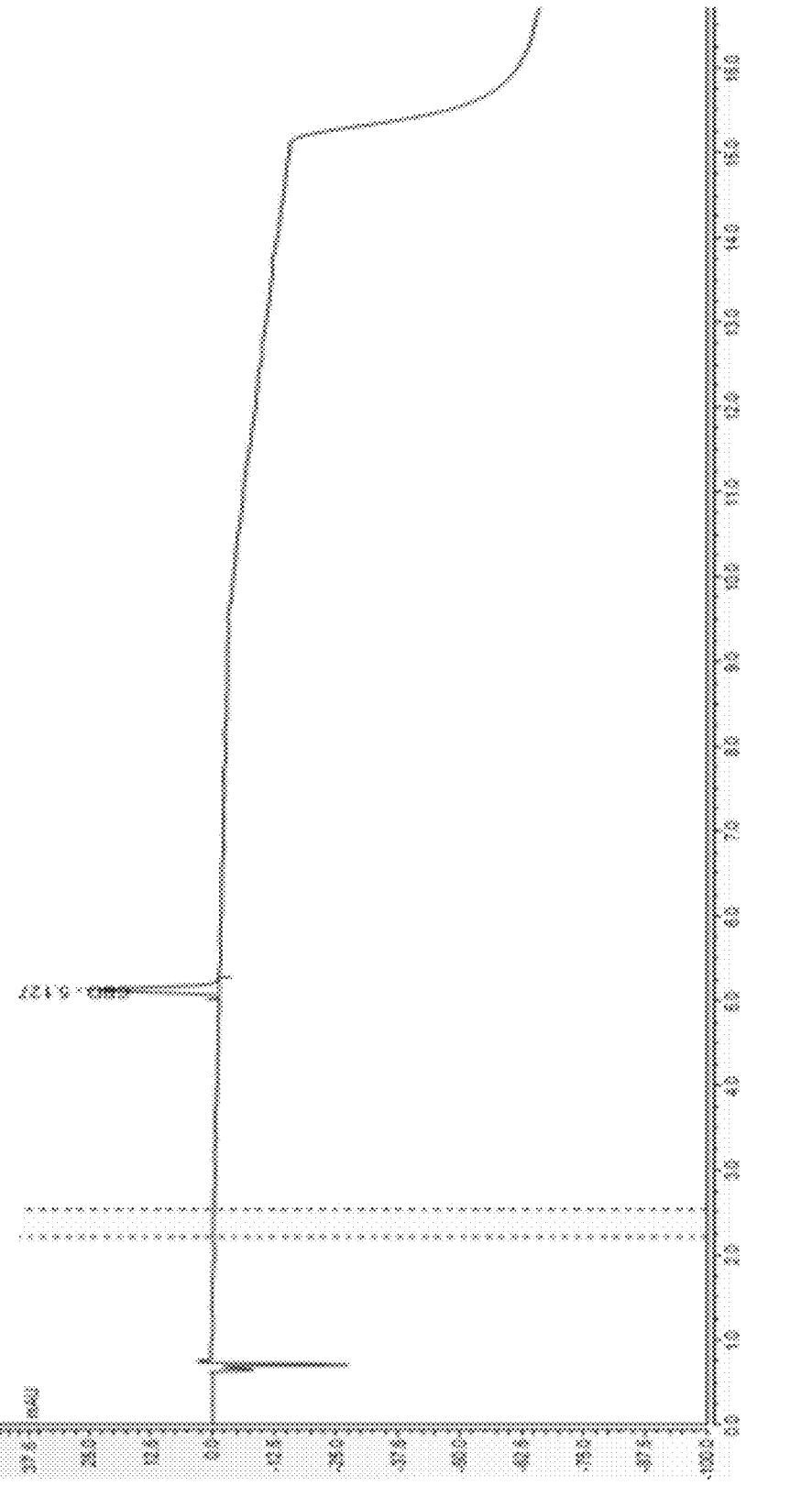

FIG. 7B. Typical HPLC chromatographic results for 10% total CBD content in micro-encapsulated Hemp oil materials of diluted digested samples after extraction and release from the encapsulated matrix (as per micro emulsion shown in Table 5, 6, 7 and 8).

Figure 8:
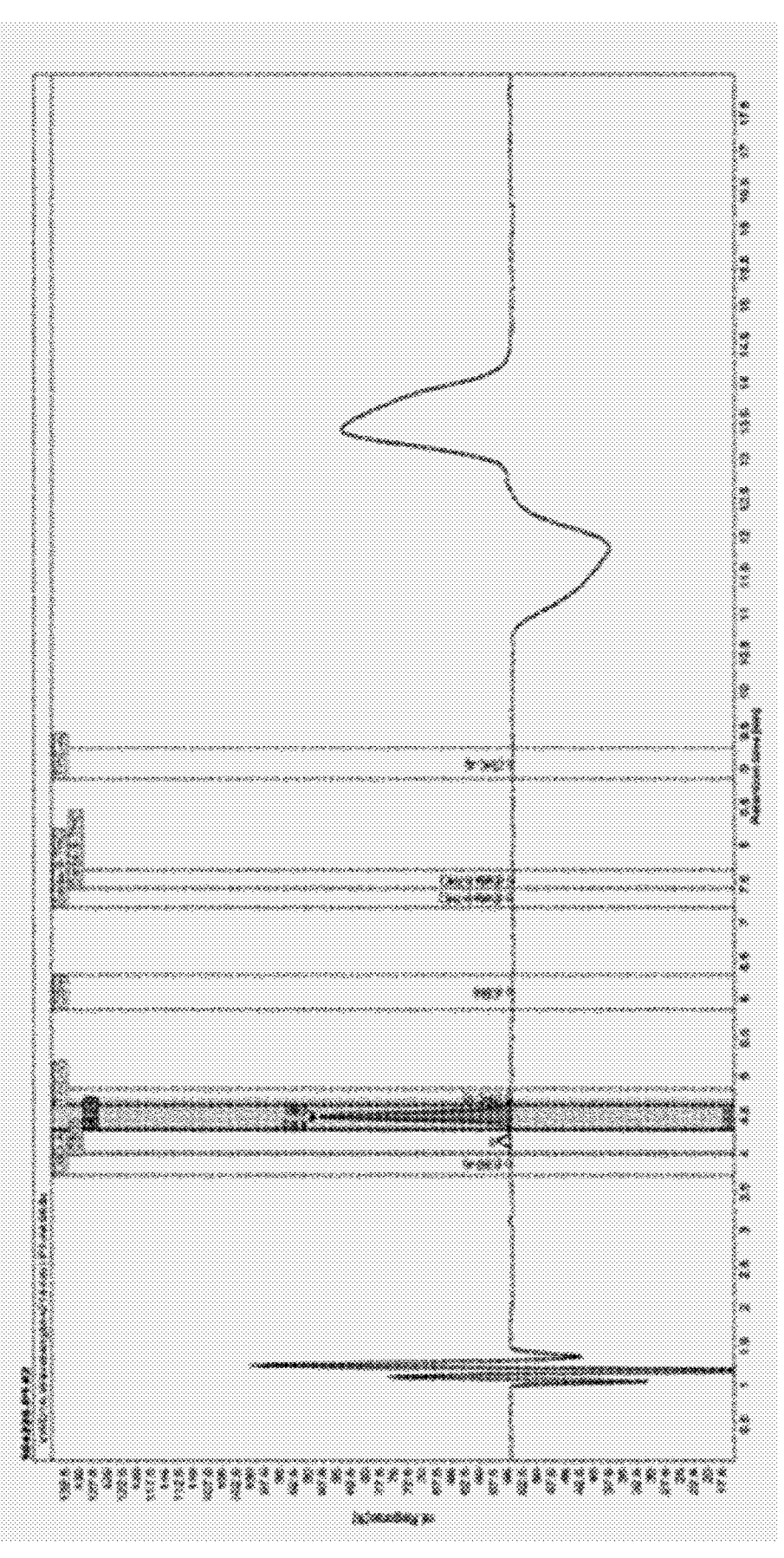

FIG. 8. HPLC chromatographic results for Hemp oil raw material used for the generation of the encapsulated matrix (raw material HPLC results for material used for micro emulsion shown in Table 1-4).

Figure 9:
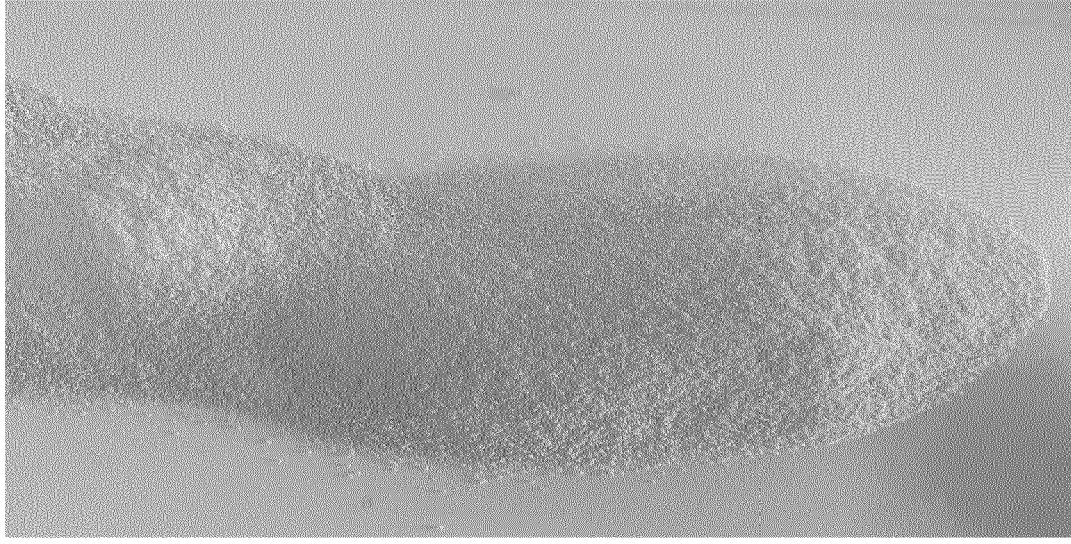

FIG. 9: 5 CBD % as per Table 2; particle size 300 um.

Figure 10:
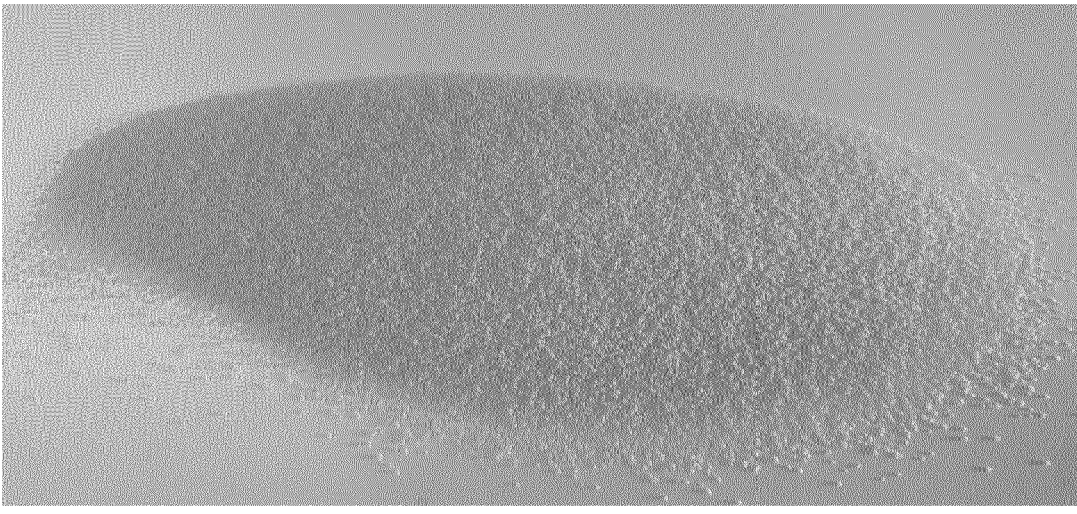

FIG. 10: 10 CBD % as per Table 8; particle size 300 um.

Figure 11:
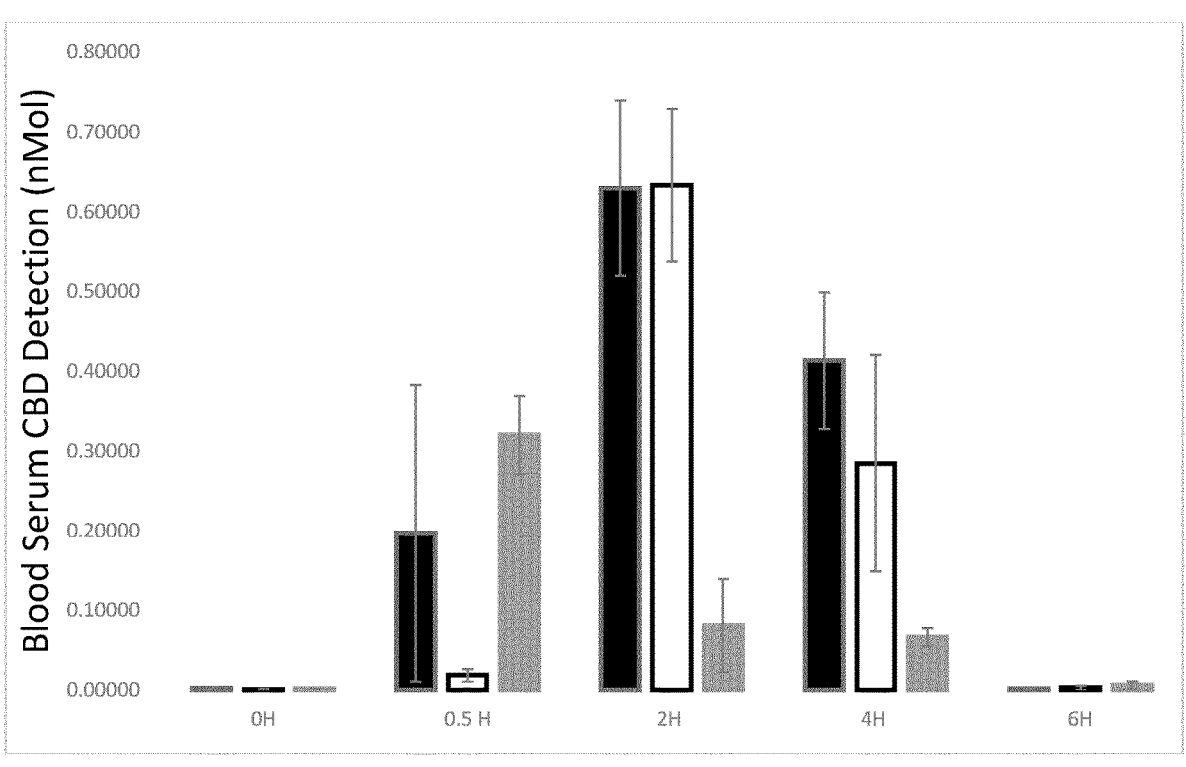

FIG. 11: Pharmakinetic (pKa) profile for encapsulated CBD relative to liposomal CBD as a function of time (6 H) after consumption (n=16). Single-centre, double-blinded randomized study. Black and white columns represent encapsulated CBD treatments with and without cyclodextrin, respectively. The grey column represents the same dose of CBD, delivered via liposomes.

Figure 12:
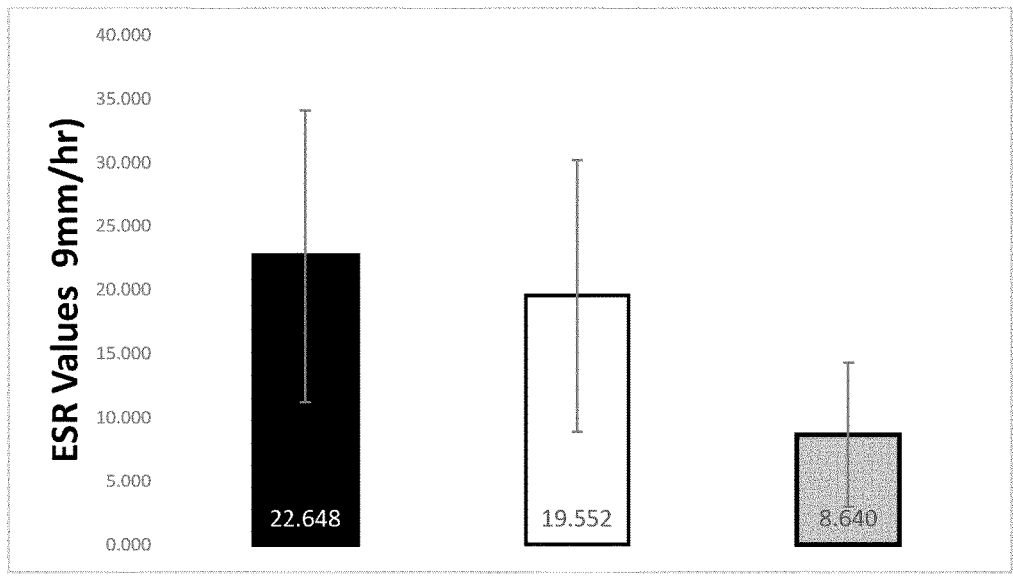

FIG. 12: Comparison of ESR percent reduction in inflammatory response for encapsulated CBD relative to liposomal CBD (n=16). Single-centre, double-blinded randomized study. The black and white columns represent encapsulated CBD treatments with and without cyclodextrin, respectively. The grey column represents the same dose of CBD, delivered via liposomes.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras;

food animals such as cows, pigs, and sheep; ungulates such as deer and giraffes;

and rodents such as mice, rats, hamsters and guinea pigs.

In preferred embodiments, the subject is a human.

"Microparticle": means a discrete particle having an average dimension in the range of 100-1000 microns, preferably X to Y microns as determined using Particle Size Distribution Assays such as Mastersizer (https://www.beckman.com/landing/ppc/part/particle-size-analysis?utm_source=google&utm_medium=cpc&gclid=CjwKCAiAp4KCBhB6EiwAx RxbpMFmJOGVaZyoub_OJqFGiFy2Lyq6CxCI9D1bw7iZ PvaAoDlp12ecJhoCRhEQA vD_BwE) The microparticle has a continuous phase comprising acacia fibre (optionally including cyclodextrin and/or maltodextrin) and dispersed phase of microdroplets of oil stabilized within the continuous phase. The oil is stabilized from oxidation within the microparticle. The microparticle also masks the smell of the oil.

"Preparation of microparticles" means a powder which consists essentially of the microparticles (it may also contain some moisture and minor amounts of free oil). Typically, preparation contains less than 10%, 9%, 8%, 7% or 6% free oil. Typically, the preparation is free flowing. Typically, the microparticles constitute at least 96%, 97%, 98% or 99% of the preparation.

"Free oil" as applied to a powder means that amount of CBD oil in the powder that is not encapsuled in a microparticle. Thus is a given powder has a free oil content of 5% by weight, this means that 95% by weight of the CBD oil in the powder is encapsuled in the microparticles (and therefore stabilized against oxidation) and 5% by weight is "free", i.e. not encapsulated and therefore not stabilized.

"Gastro-resistant": means that the microparticles can survive intact for at least 60 minutes in the simulated stomach digestion model described in Minekus et al., 1999 and 2014 (A computer-controlled system to simulate conditions of the large intestine with peristaltic mixing, water absorption and absorption of fermentation product, Minekus, M., Smeets-Peeters M, Bernalier A, Marol-Bonnin S, Havenaar R, Marteau P, Alric M, Fonty G, Huis in't Veld J H, Applied Microbiology Biotechnology. 1999 December; 53 (1):108-14) and (Minekus et al., 2014, A standardised static in vitro digestion method suitable for food—an international consensus, Minekus, A. et al., Food Function, 2014, 5, 1113).

"Ileal-sensitive": means that the microencapsulates are capable of releasing their contents in vivo in the ileum of a mammal.

"CBD oil" (also referred to as "Hemp oil") refers to an oil or extract fraction derived from any part of the hemp plant of the *Cannabis Sativa* L. family. It generally contains less than 0.2% tetrahydrocannabinol (THC) (w/w) and 2-96% of cannabidiol (CBD). The CBD oil employed in the process and products of the present invention may be obtained from hemp seeds, or from hemp plant matter, or both. The process of the invention provides hemp oil in a microparticle in a stabilized from, in which the cannabinoid content of the oil is high, for example providing for more than 40 or 50 mg/g in encapsulates microparticles.

"Cannabidiol" or "CBD" refers to a specific cannabinoid present in CBD oil. It is described in Mechoulam et al (Journal of Clinical Pharmacology, (2002) 42 (11 Suppl)). Rustichelli et al 1998 describes how direct gas chromatography (GC) analysis can only determine the total cannabinoid content of plant tissue extracts. This is due to the acidic cannabinoid compounds being converted to neutral cannabinoids by high temperatures when injected into a GC system. High performance liquid chromatography (HPLC) can detect both the acidic and neutral forms of cannabinoids. This paper outlines a room temperature method of analysis with a mobile phase of methanol/water in the ration of 80:20 (v/v). The flow rate was set to 1.0 ml/L min-1 and the injection volume was 20.0 μL. A mass spectrophotometer (MS) was also used as a method of detection. The mass range of m/z 45-700 was scanned once per second. The following parameters were set on the MS; the electron impact (EI) mode was enabled, ionization energy 70 eV; ion source temperature 250° C., filament current 200 ρA, conversion dynode power −15 kV and electron multiplier voltage 1500V. To accurately and directly measure the presence of CBD (Cannabidiol), CBD-A (Cannabidiol-A), THC (Tetrahydrocannabinol), CBCh (Cannabichromene) and total cannabinoids by using HPLC-MS. A HPLC-UV with an ultra violet detector array set at 220 nm with 0.04 absorbance full scale is commonly used to measure cannabinoid content. The Equipment needed included HPLC Agilent Infinity 1260 (Column: Zorbax® Eclypse C18, 5 μm, 250× 4.6 mm (Agilent); solvent system: Methanol, H2O, acetic acid. Isocratic Detector: Diode array −220 nm. HPLC/DAD method can also be used (References: De Backer, B., Debrus, B., Lebrun, P., Thenunis, L., Dubois, N., Decock, L., Verstraete, A., Hubert, P. and Charlier, C. (2009) Innovative development and validation of an HPLC/DAD method for the qualitative and quantitative determination of major cannabinoids in *cannabis* plant material. Journal of Chromatography B, 877(2009) 4115-4124.

"Microemulsion" means a CBD oil emulsion that is formed between CBD oil, an aqueous phase (e.g. water), acacia or inulin fibre optionally in combination with another filler such as maltodextrin or protein, and optionally an emulsifier. An emulsifier is generally not essential as acacia or inulin fibre contains natural surfactants. In one embodiment, the microemulsion comprises CBD oil, an aqueous phase, acacia fibre and optionally a filler such as maltodextrin or cyclodextrin. It is a generally clear (non-turbid) and thermodynamically stable emulsion that does not require high shear for its formation. The microemulsion is formulated with an aqueous phase (e.g. water) and solids (oil, acacia or inulin fibre and optionally other components such as maltodextrin). The microemulsion contains about 20 to about 60% solids and about 40 to about 80% aqueous phase, preferably about 25 to about 50% solids and about 50 to about 75% aqueous phase, and more preferably about to about 40% solids and about 60 to about 70% aqueous phase (weight to weight). The ratio by weight of CBD oil to acacia or inulin fibre in the solids may be about 1:4 to 4:1, about 1:3 to 3:1 or about 1:2 to 2:1. The solids generally comprise 25-75% CBD oil and 25-75% acacia or inulin fibre (or acacia/inulin fibre and a filler such as maltodextrin). The solids typically comprise 20-60% CBD oil and 25-75% acacia/inulin fibre (or acacia/inulin fibre and a filler such as maltodextrin). A surfactant may be included and generally constitutes less than 5% of the solids. Generally, all of the components of the microemulsion have GRAS (generally recognized as safe) status (https://www.fda.gov/food/food-ingredients-packaging/generally-recognized-safe-gras).

"Microdroplet" as applied to the CBD oil in the microparticle means a discrete droplet of CBD oil having an average dimension of 20-500 microns and as applied to oil in the microparticle means a discrete droplet of oil having an average dimension in the nanometer or micron range, suitably of less than 300 or 200 microns and ideally of microns to 150 microns.

"Loading content" as applied to oil and the method of the invention refers to the amount of CBD oil that is used in the process compared to the amount of CBD oil that is retained in the preparation of microparticles produced by the method.

"Fibre" refers to a soluble fibre (e.g. at least 85% soluble fibre by weight) typically having a viscosity of of 550-900 cp at 10% v/w. Examples include acacia fibre and inulin fibre. "Acacia fibre" refers to a fibre obtained from the sap of the Acacia tree. It is also known as gum Arabic. It is often provided as a powder. "Inulin" refers to a soluble fibre that is a type of prebiotic. It's not digested or absorbed in the stomach. It stays in the bowel and helps certain beneficial bacteria to grow. Inulin is a starchy substance found in a wide variety of fruits, vegetables, and herbs, including wheat, onions, bananas, leeks, artichokes, and asparagus. The inulin that is used in supplements most commonly comes from soaking chicory roots in hot water.

"Emulsifier" refers to a surfactant suitable for forming a microemulsion. It is optional in the method and products of the invention. An example is lecithin, for example sunflower lecithin. Generally, the surfactant is employed as a minor amount (e.g. less than 5%, 4%, 2%, 2% or about 1% of the microemulsion). Other emulsifiers include mono and diglycerols, locust bean gum and xanthan gum.

"Cyclodextrin" refer to a member of the family of cyclic oligosaccharides, consisting of a macrocyclic ring of glucose subunits joined by α-1,4 glycosidic bonds. Cyclodextrins are produced from starch by enzymatic conversion. Cyclodextrins are composed of 5 or more α-D-glucopyranoside units linked 1->4, as in amylose (a fragment of starch). The largest cyclodextrin contains 32 1,4-anhydroglucopyranoside units, while as a poorly characterized mixture, at least 150-membered cyclic oligosaccharides are also known. Typical cyclodextrins contain a number of glucose monomers ranging from six to eight units in a ring, creating a cone shape.

"Treating the microemulsion to remove water and provide a preparation of dried microparticles" means drying the microemulsion to provide a solid microemulsion cake and optionally size-reducing the solid. Treatments include freeze-drying or vacuum drying followed by size reduction, or spray drying, to provide the preparation of microparticles.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Formation of Microemulsion

TABLE 1

| | |
|---|---|
| CBD oil | 40 g |
| Sunflower lecithin | 1 g |
| Cyclodextrin | 60 g |
| RO water | 200 ml |

TABLE 2

| | |
|---|---|
| CBD Oil | 70 g |
| Sunflower lecithin | 1 g |
| Cyclodextrin | 30 g |
| Calcium Citrate | 5 g |

TABLE 3

Generation of CBD micro-encapsulated powder - 5% Cannabidiol (CBD)

| Ingredient | Quantity (Gram) | Percent of T. Solids |
|---|---|---|
| Water | 28,093.29 | |
| Acacia Fibre | 9,364.43 | 55.39 |
| CycloDextrin | 0.00 | |
| Maltodextrin | 1,872.89 | 11.08 |
| Hemp Oil | 5,669.39 | 33.53 |
| Total solids Content (Gram) | 16906.71 | |
| Total weight Including water (Gram) | 45000.00 | |
| Total solids % | | 37.57% |

TABLE 4

Generation of CBD micro-encapsulated powder - 5% Cannabidiol (CBD)

| Ingredient | Quantity (Gram) | Percent of T. Solids |
|---|---|---|
| Water | 30,000 | |
| Acacia Fibre | 3,000 | 21.37 |
| CycloDextrin | 5,000 | 35.61 |
| Maltodextrin | 1,000 | 7.12 |
| Hemp Oil | 5,040 | 35.90 |
| Total solids Content (Gram) | 14040.11 | |
| Total weight Including water (Gram) | 44,040.11 | |
| Total solids % | | 31.90% |

TABLE 5

Generation of CBD micro-encapsulated powder with oligosaccharide filler - 10% Cannabidiol (CBD)

| Ingredient | Quantity (KGram) | Percent of T. Solids |
|---|---|---|
| Water | 28.00 | |
| Acacia Fibre | 5.50 | 28.95 |
| CycloDextrin | 0.00 | |
| Maltodextrin | 1.50 | 7.89 |
| Hemp Oil | 12.00 | 63.16 |
| Total solids Content (KGram) | 19.00 | |
| Total weight Including water (KGram) | 47.00 | |
| Total solids % | | 40.43% |

TABLE 6

Generation of CBD micro-encapsulated powder with oligosaccharide filler - 10% Cannabidiol (CBD)

| Ingredient | Quantity (KGram) | Percent of T. Solids |
|---|---|---|
| Water | 30.0 | |
| Acacia Fibre | 2.0 | 11.43 |
| CycloDextrin | 4.0 | 22.86 |
| Maltodextrin | 1.0 | 5.71 |
| Hemp Oil | 10.5 | 60.00 |
| Total solids Content (Gram) | 17.50 | |
| Total weight Including water (Gram) | 47.50 | |
| Total solids % | | 36.84 |

TABLE 7

Generation of a high loaded CBD micro-encapsulated powder - 10% Cannabidiol (CBD)

| Ingredient | Quantity (KGram) | Percent of T. Solids |
|---|---|---|
| Water | 1280.00 | |
| Acacia Fibre | 205.00 | 27.70 |
| Maltodextrin | 45.00 | 6.08 |
| Hemp Oil | 490.00 | 66.22 |
| Total solids Content (KGram) | 740.00 | |
| Total weight Including water (KGram) | 2020.00 | |
| Total solids % | | 36.63% |

TABLE 8

Generation of a high loaded CBD micro-encapsulated
powder - 10% Cannabidiol (CBD)

| Ingredient | Quantity K(Gram) | Percent of T. Solids |
|---|---|---|
| Water | 1,280.00 | |
| Acacia Fibre | 110.00 | 17.32 |
| CycloDextrin | 110.00 | 17.32 |
| Maltodextrin | 15.00 | 2.36 |
| Hemp Oil | 400.00 | 62.99 |
| Total solids Content (KGram) | 635.00 | |
| Total weight Including water (KGram) | 1,915.00 | |
| Total solids % | 33.16 | |

TABLE 9

Generation of a high loaded CBD micro-
encapsulated powder - 75% CBD

| INGREDIENT | KG | % Solids |
|---|---|---|
| Water | 47 | |
| Acacia Fibre | 0 | 0.00 |
| Cyclodextrin | 6.5 | 19.70 |
| Maltodextrin | 1.5 | 4.55 |
| Hemp Oil | 25 | 75.76 |
| | | 100.00 |
| Total Solids KG | 33 | |
| TOTAL + Water | 80 | |
| TOTAL solids % | 41.25 | |

TABLE 10

Generation of a Medium loaded CBD
micro-encapsulated powder - 25% CBD

| INGREDIENT | KG | % Solids |
|---|---|---|
| Water | 58 | |
| Acacia | 0 | 0.00 |
| Cyclodextrin | 30 | 70.67 |
| Maltodextrin | 1.45 | 3.42 |
| Hemp Oil | 11 | 25.91 |
| | | 100.00 |
| Total Solids KG | 42.45 | |
| TOTAL + Water | 100.45 | |
| TOTAL solids % | 42.26 | |

TABLE 11

Generation of a High loaded CBD micro-
encapsulated powder - 40% CBD

| INGREDIENT | KG | % Solids |
|---|---|---|
| Water | 55 | |
| Acacia Fibre | 0 | 0.00 |
| Cyclcodextrin | 15 | 50.00 |
| Maltodextrin | 3 | 10.00 |
| Hemp Oil | 12 | 40.00 |
| | | 100.00 |
| Total Solids KG | 30 | |
| TOTAL + Water | 85 | |
| TOTAL solids % | 35.29 | |

Food Applications

| EXAMPLE 1: GUMMIE | 25 mg CBD micro-encapsulated powder 3.5 gram pectin gummie |
|---|---|

-continued

| EXAMPLE 2: GUMMIE | 20 mg CBD micro-encapsulated powder 5 gram pectin gummie |
|---|---|
| EXAMPLE 3: BEVERAGE | 50 mg CBD micro-encapsulated powder 350 ml carbonated lemonade |
| EXAMPLE 4: BEVERAGE | 100 mg CBD micro-encapsulated powder 500 ml carbonated cherry beverage |
| EXAMPLE 5: SACHET | 50 mg CBD micro-encapsulated powder 7.5 gram Maltodextrin 50 mg sweetener and flavour |

TABLE 12

Gummie Preparation

| INGREDIENTS | FUNCTION | PROPORTION(%) |
|---|---|---|
| Soluble Fibre | Bulking Agent | 50 |
| Sweetener | Sweetening Agent | 25 |
| Purified Water | Carrier | 15.5-15.9 |
| Pectin | Gelling Agent | 5.0 |
| Citric Acid | Acidifying Agent | 3.00 |
| Natural Flavor | Flavoring Agent | 1.00 |
| CBD | Active | 0.10-0.50 |
| Total | | 100% |

Formation of Microparticles

Hydration of Biopolymers

Weight water and heat to 60° C.

Disperse half the required quantity of acacia gum in the tempered water.

Add acacia powder slowly and allow material to hydrate before adding more.

Homogenise using single or three stage homogenisation for minimum 5 minutes

Allow the material to rest for minimum 5 minute

Add the Maltodextrin material

Homogenise using single or three stage homogenisation for 3 minutes at 10,000 rpm Add remaining acacia gum material Homogenise for minimum 3 −5 minutes Allow to dispersion to mix using a stir bar mild agitation for 20 min until all material is fully hydrated and dispersed Remove vessel from 60° C. heat and allow to cool to Room Temperature Addition of Hemp Oil Add Hemp Oil to the vessel while it is under mil agitation Add oil drop-by-drop while solution is agitating fast using sit bar Do not high shear mix Once all the hemp oil is added Homogenize using single or three stage homogenisation for minimum 10 minutes.

Leave the solution stirring overnight

Ideally 6-8 hours at room temperature (20° C.)

The mixture is then homogenized through single or three stage homogenizer twice for minimum 10 minutes.

Generation of Micro-Emulsion

After the overnight storage step, homogenize using single or three stage homogenisation at room temperature for 10 minutes.

Allow the solution resting time for minimum 5 minutes.

Repeat homogenisation steps using single or three stage homogenisation for minimum 10 minutes Keep solution under mild agitation (350 rpm/Room Temperature) while freeze drier is being filled The formed microemulsion is poured into a tray at a depth of 1 cm Freeze-Drying—Pro-cool Tray: Set temperature of trays to −50° C. for 90 minutes in semi-automatic mode. This mode is commonly used to freeze the product. The equipment will maintain the shelf temperature until another action is operated. Typical Cool Down ratio for commercial lyophilizer for 20° C. to −40° C. in 60 minutes. Thereafter, addition time is needed to cool from −40° C. to −50° C. in 30 minutes; hence total time for cooling 90 minutes.

Freeze-Drying—Pro-Cool Tray

Set temperature of trays to −50° C. for 90 minutes in semi-automatic mode. This mode is commonly used to freeze the product. The equipment will maintain the shelf temperature until another action is operated.

Typical Cool Down ratio for commercial lyophilizer for 20° C. to −40° C. in 60 minutes.

Thereafter, addition time is needed to cool from −40° C. to −50° C. in 30 minutes; hence total time for cooling 90 minutes.

Primary Drying: this initiates the main drying step. Input is required for temperature controlling for the shelves vacuum level. The equipment will maintain these values until another action is operated. The initial drying steps. can be summarised as follows:

Set conditions for 2 h at −25° C. and 0.1 mbar

Set temperature ramp from −25° C. to −10° C. in 2 h and 0.1 mbar

Subsequently set for 2 h at −10° C. and 0.1 mbar

Set temperature ramp from −10° C. to 0° C. in 2 h and 0.1 mbar

Temperature ramp from 0° C. to 10° C. in 2 h and 0.1 mbar

Temperature ramp from 10° C. to 20° C. in 4 h and 0.1 mbar

Secondary drying: this initiates removal of remaining moisture from the concentrate after completion of primary drying. by controlling the shelves to the required temperature and vacuum level.

Temperature ramp from 20° C. to 30° C. in 12 h and 0.1 mbar

Temperature ramp from 30° C. to 37.5° C. in 20 h and 0.1 mbar

Size Reduction: Emulsion cake from freeze drying tray is size reduced in a commercial grinder before being sieved to an average particle dimension of 300-500 μm.

Clinical Study 1

A human intervention trial was performed with ethical approval to evaluate micro-encapsulation for enhanced bioavailability of CBD (two different formats) relative to liposomal CBD formats.

Type of study: Single-centre, double-blinded randomized study.

Aim: This study seeks to demonstrate efficient delivery of micro-encapsulated CBD, while also validating the protective properties of encapsulation during transit through the body with subsequent release in the intestine, for potential absorption into the blood stream with slow release effects.

Endpoint: Appearance of CBD in peripheral blood plasma. Participants were blinded with regard to intervention or control; all samples are provided in the form of non-descript bottles for consumption.

Samples: Blood samples taken on Day 0 at specific time intervals: Time 0, 0.5 h, 2 h, 4 h, 6 h after consumption of the test drink (CBD in 500 ml water). Day 28 assessment will be conducted thereafter with one timepoint. Each participant would represent their own control (time 0) and participants are randomised.

Study Power & Recruitment: Based on the proposed design, 17 participants were recruited allowing liposomal and micro-encapsulated materials to be compared (two encapsulation formats under review)

Data generated from a human intervention study (FIG. 11), demonstrated that

Three times (×3) as much CBD is absorbed into the blood when equal amounts of Micro-encapsulated CBD are ingested compared to Liposomal CBD Peak blood CBD levels for Micro-encapsulated CBD are almost twice that observed for liposomal CBD Micro-Encapsulated CBD is absorbed into the blood slower than liposomal CBD: hence controlled release pharmacokinetics are observed CBD was detected with liposomal 30 minutes after ingestion; as opposed to 75 minutes with encapsulated CBD Clinical Study 2

CBD: It has been reported to improve learning and memory, and to reduce inflammation. However, the role of CBD in enhancing the immune response remains unclear. Serum C-reactive protein (CRP) is a marker of systemic inflammation, and is elevated in the presence of chronic conditions, including cardiovascular diseases, obesity, type 2 diabetes and several components of the metabolic syndrome including high blood pressure, high waist circumference, fasting blood glucose low serum high-density lipoprotein cholesterol, and raised triacylglycerol. This presented study investigated if encapsulation could accelerate immuno-modulatory responses i.e. specifically anti-inflammatory properties.

Blood tests are used to assess if a person has inflammation. Cannabis use is associated with lower levels of C reactive protein (CRP), but only among those whose CRP levels were below the median. In order to assess inflammatory response in broader populations, ESR (erythrocyte sedimentation rate) tests were utilised.

The ESR Inflammatory test measures the rate at which red blood cells separate from the plasma. A blood sample is taken from the participant in the study and put in a tube that contains a chemical to stop the blood from clotting. The tube is left to stand upright. The red blood cells (erythrocytes) gradually fall to the bottom of the tube (as a sediment). The clear liquid plasma is left at the top. The ESR measures the rate at which the red blood cells separate from the plasma and fall to the bottom of a test tube. The rate is measured in millimetres per hour (mm/hr). This is easy to measure as there will be a number of millimetres of clear liquid at the top of the red blood after one hour.

When inflammatory markers were compared between participants who consumed encapsulated and liposomal CBD, the following conclusions were made (FIG. 12):

After 28 days supplementation, the average ESR blood biomarker values were reduced for all treatments (encapsulated and Lipsomal treatments)

The greatest reduction in ESR values was recognised for participants who consumed encapsulated treatments (>22%)

No significant differences in ESR reduction were evident between encapsulation treatments with and without cyclodextrin The immunomodulatory response is least effective with liposomal treatments The encapsulation treatments with and without cyclodextrin have the potential to regulate the immune system through the immunomodulatory properties delivered by CBD.

Attenuation of immunomodulatory responses is greatest with encapsulation technology relative to liposomal formats

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of making a food, beverage or nutritional supplement composition comprising a preparation of gastro-resistant, ileal-sensitive, microparticles, the method comprising the steps of:

providing an oil-in-water microemulsion comprising an aqueous phase and a solid phase comprising CBD oil and acacia or inulin fibre;

freeze-drying the microemulsion to provide a solid cake; and size-reducing the cake to provide the preparation of gastro-resistant, ileal-sensitive microparticles, wherein:

the microparticles comprise a dispersed phase of stabilized microdroplets of CBD oil disposed in a continuous solid matrix comprising acacia or inulin fibre;

the preparation of microcapsules contains less than 10% free CBD oil; and the oil-in-water microemulsion is formed by a process comprising the steps of:

(a) combining water with acacia or inulin fibre and allowing the acacia or inulin fibre to hydrate;

(b) homogenizing the hydrated fibre;

(c) adding the CBD oil to the homogenized hydrated fibre to form a mixture;

(d) homogenizing the mixture;

(e) allowing the homogenized mixture to rest for a resting time of at least 5 minutes; and (f) repeating steps (d) and (e) in sequence.

2. A method according to claim 1, in which the solid phase comprises 2-15% maltodextrin (w/v).

3. A method according to claim 1, in which the solid phase comprises cyclodextrin, and in which a weight ratio of acacia or inulin fibre to cyclodextrin is at least 2:1.

4. A method according to claim 1, in which the microemulsion comprises 10-70% of the solid phase and 30-90% of the aqueous phase (w/w).

5. A method according to claim 1, in which the microemulsion comprises 20-30% of the solid phase and 70-80% of the aqueous phase (w/w).

6. A method according to claim 1 in which the solid phase comprises 25-70% by weight CBD oil.

7. A method according to claim 1 in which the solid phase comprises 25-70% by weight CBD oil, maltodextrin and/or cyclodextrin.

8. A method according to claim 1, including repeating steps (d) and (e) in sequence at least two times.

9. A method according to claim 1, in which a homogenisation pressure during the rounds of homogenization/resting is alternated between a low pressure of 30-70 Pa and a high pressure of 130-170 Pa.

10. A food, beverage or nutritional supplement composition comprising a powder, in which the powder comprises freeze dried microparticles and less than 10% free CBD oil, in which the freeze dried microparticles comprise CBD oil and acacia or inulin fibre in which the CBD oil is provided as stabilized CBD oil microdroplets distributed throughout a continuous solid matrix comprising acacia or inulin fibre.

11. A food, beverage or nutritional supplement composition according to claim 10, in which the continuous solid matrix comprises an oligosaccharide filler selected from cyclodextrin and maltodextrin in which a weight ratio of fibre to oligosaccharide filler is at least 2:1.

12. A food, beverage or nutritional supplement composition according to claim 10, in which the microparticles have an average dimension of 150-500 microns.

13. A food, beverage or nutritional supplement composition according to claim 10, in which the microparticles have an average dimension of 150-500 microns and in which the powder contains 3-12% stabilized CBD oil.

14. A food, beverage or nutritional supplement composition according to claim 10, in which a weight ratio of fibre to oligosaccharide filler is at least 3:1.

15. A food, beverage or nutritional supplement composition according to claim 10, comprising 2-15% maltodextrin by weight.

16. A food, beverage or nutritional supplement composition according to claim 10, consisting essentially of CBD oil, acacia or inulin fibre, an oligosaccharide filler, less than 10% free CBD oil, and less than 5% moisture.

17. A food, beverage or nutritional supplement composition according to claim 10, having less than 7% free CBD oil.

18. A food, beverage or nutritional supplement composition according to claim 10 that is an aqueous beverage comprising 1-20% by weight of the powder, in which the continuous solid matrix of the microparticles comprises maltodextrin.

19. A food, beverage or nutritional supplement composition according to claim 10, in which the composition is a gummie.

* * * * *